United States Patent [19]

Hamanaka

[11] Patent Number: 4,614,737

[45] Date of Patent: Sep. 30, 1986

[54] 2-DIOXACYCLOALKYLTHIOPENEM DERIVATIVES

[75] Inventor: Ernest S. Hamanaka, Gales Ferry, Conn.

[73] Assignee: Pfizer Inc., New York, N.Y.

[21] Appl. No.: 649,517

[22] Filed: Sep. 13, 1984

Related U.S. Application Data

[63] Continuation-in-part of Ser. No. 541,854, Oct. 14, 1983, abandoned.

[51] Int. Cl.$^4$ .................. C07D 499/00; A61K 31/425
[52] U.S. Cl. .................................... 514/193; 540/310; 514/192
[58] Field of Search ................. 260/245.2 R, 245.2 T; 514/192, 193, 194

[56] References Cited

U.S. PATENT DOCUMENTS 4,260,618  4/1981  Christensen et al. ............... 514/192

Primary Examiner—Nicholas S. Rizzo
Attorney, Agent, or Firm—Charles J. Knuth; Albert E. Frost; Robert K. Blackwood

[57] ABSTRACT

Certain 2-dioxacycloalkylthio-2-penem-3-carboxylic acid compounds are useful as antibacterials for treating mammals and have the formula

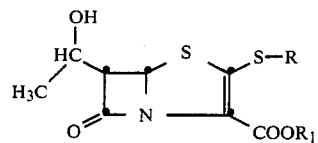

or a pharmaceutically acceptable salt thereof, wherein:
R is

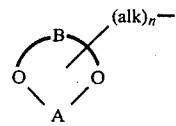

A is carbonyl, methylene or thiocarbonyl;
B is alkylene having 2–5 carbon atoms;
alk is alkylene having 1–6 carbon atoms;
$R_1$ is hydrogen or a group which results in an ester which is hydrolyzable in vivo; and
n is zero or one.

42 Claims, No Drawings

2-DIOXACYCLOALKYLTHIOPENEM DERIVATIVES

CROSS-REFERENCE TO RELATED APPLICATION

This application is a continuation-in-part of Ser. No. 541,854, filed Oct. 14, 1983 now abandoned.

BACKGROUND OF THE INVENTION

This invention is directed to a family of antibacterial agents incorporating a 2-azetidinone (beta-lactam) ring. Chemically, the antibacterial agents of this invention are identified as 6-alpha-1-hydroxyethyl-2-substituted-2-penem-3-carboxylic acid compounds.

Although certain 2-substituted-2-penem-3-carboxylic acid compounds have been previously disclosed, there is a continuing need for novel compounds having desirable antibacterial therapeutic properties.

SUMMARY OF THE INVENTION

The present invention is directed to a compound of the formula

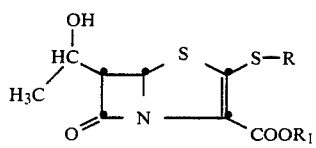

or a pharmaceutically acceptable salt thereof, wherein: R is

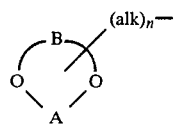

A is carbonyl, methylene or thiocarbonyl;
B is alkylene having 2-5 carbon atoms;
alk is alkylene having 1-6 carbon atoms;
$R_1$ is hydrogen or a group which results in an ester which is hydrolyzable in vivo; and
n is zero or one.

Included within the scope of the present invention is a compound of the formula

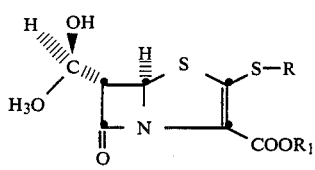

or a pharmaceutically acceptable salt thereof, wherein: R and $R_1$ are as defined above for compounds of formula I.

Preferred compounds of formula I or II include those wherein $R_1$ is hydrogen, B is ethylene, A is methylene and n is one; particularly when R is 1,3-dioxacyclopent-4-ylmethyl or 1,3-dioxacyclopent-2-ylmethyl.

Also preferred are compounds of formula I or II wherein $R_1$ is hydrogen, B is ethylene, A is carbonyl, n is one and alk is methylene; particulary when R is 2-oxo-1,3-dioxacyclopent-4-ylmethyl.

Further preferred are compounds of formula I or II wherein $R_1$ is hydrogen, B is propylene, A is methylene and n is zero; particularly when R is 1,3-dioxacyclohex-5-yl.

Additionally preferred are compounds of formula I or II wherein $R_1$ is hydrogen, B is propylene, A is carbonyl and n is zero; particularly when R is 2-oxo-1,3-dioxacyclohex-5-yl.

Further embraced by the present invention is a pharmaceutical composition comprising a compound of formula I or II and a pharmaceutically acceptable diluent or carrier and a method of treating a bacterial infection in a mammal comprising administering an antibacterially effective amount of a compound of formula I or II.

DETAILED DESCRIPTION OF THE INVENTION

The compounds of formulas I and II are useful as antibacterial agents, and are derivatives of the bicyclic nucleus of the formula:

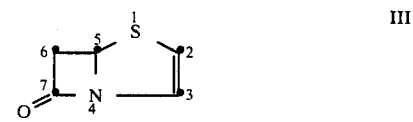

Throughout this specification, the nucleus of formula III is identified by the name "2-penem," and ring atoms are numbered as shown. The carbon atom attached to ring carbon 6 is given the number 8. Also, throughout this specification, the abbreviation "PNB" is used for the p-nitrobenzyl group.

The relationship between the hydrogen on bridgehead carbon 5 and the remaining hydrogen on carbon 6 in compounds of formula I can either be cis or trans. The present invention embraces both isomers as well as mixtures thereof. The trans isomer is generally preferred in pharmaceutical applications and the cis isomer can be readily converted to the trans-isomer.

Generally, carbon 5 will have the absolute stereochemistry designated R using the Prelog-Ingold R,S stereochemical notation, which is employed in this application. Thus, for example, a compound of formula II wherein R is 1,3-dioxacyclohex-5-yl and $R_1$ is hydrogen is named (5R,6S)-6-[(R)-1-hydroxyethyl]-2-(1,3-dioxacyclohex-5-yl)thio-3-carboxyl-2-penem.

As will be appreciated, various optically active isomers of the new compounds are possible. The present invention embraces such optically active isomers as well as mixtures thereof.

The present invention is directed to penems substituted in the 2-position by a moiety of the general formula R—S—.

The present invention includes those penems in which the 3-carboxyl group is esterified with a nontoxic ester group which is hydrolyzed in vivo. These esters are rapidly cleaved in mammalian blood or tissue to release the corresponding penem-3-carboxylic acid. Typical examples of such readily hydrolyzable ester-forming residues are alkanoyloxymethyl having from 3-8 carbon atoms, 1-(alkanoyloxy)ethyl having from 4-9 carbon atoms, 1-methyl-1-(alkanoyloxy)ethyl having from 5-10 carbon atoms, alkoxycarbonyloxymethyl having from 3-6 carbon atoms, 1-(alkoxycarbonyloxy)ethyl having from 4-7 carbon atoms, 1-methyl-1-(alkoxycarbonyloxy) ethyl having from 5-8 carbon atoms, N-(alkoxycarbonyl) aminomethyl having from 3-9 carbon atoms, 1-(N-[alkoxycarbonyl]amino)ethyl having from 4-10 carbon atoms, 3-phthalidyl, 4-crotonolactonyl, gamma-butyrolacton-4-yl, carboxyalkylcarbonyloxymethyl having from 4-12 carbon atoms or 5-methyl-2-oxo-1,3-dioxolen-4-ylmethyl.

To prepare compounds of formula I or II wherein $R_1$ is a group which forms an ester which is hydrolyzed in vivo, the acid of formula I or II ($R_1$ is hydrogen) is reacted with a base to form the corresponding anion. Suitable cations include sodium, potassium, calcium, tetra-alkylammonium and the like. The anion can be prepared by lyophilizing an aqueous solution of I or II, for example, an aqueous solution containing tetrahydrofuran, and sodium bicarbonate or tetrabutylammonium hydroxide.

The resulting anion of I or II is reacted with the corresponding chloride or bromide of $R_1$ in a reaction-inert solvent such as acetone or dimethylformamide at about 20° to about 50° C., preferably 25° C.

The compounds of formula II can be synthesized according to Schemes A–C.

As shown in Scheme A, a compound of formula II can be prepared in accordance with the procedure of Yoshida et al, *Chem. Pharm. Bull.*, 29, 2899–2909(1981), from the known dibromo penam of formula IV. The dibromo penam (IV) undergoes an exchange reaction with t-butyl magnesium chloride at a temperature of between about −90° and −40° C., preferably about −78° C. in a reaction-inert solvent such as tetrahydrofuran, diethyl ether or toluene, preferably tetrahydrofuran. Other organometallic reagents may also be employed. The resultant reaction mixture is treated in situ with the appropriate aldehyde; e.g., acetaldehyde for the 1-hydroxyethyl derivative. The aldehyde is added at between about −80° and −60° C., preferably about −78° C. for acetaldehyde.

The resulting bromo hydroxy penam V is hydrogenated to remove the 6-bromo substituent. A suitable hydrogenation catalyst is a noble metal catalyst such as palladium. The reaction is carried out in a protic solvent such as 1:1 methanol-water or 1:1 tetrahydrofuran-water, preferably 1:1 methanol-water, at a pressure of about 1 to 4 atms, preferably 4 atm and a temperature of between about 0° and 30° C., preferably about 25° C.

The resulting alcohol of formula VI can be protected with a trialkylhalosilane of formula

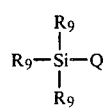

wherein $R_9$ at each occurrence is an alkyl of 1 to 6 carbon atoms and Q is chloro, bromo or iodo. Thus, dimethyl-t-butylchlorosilane in the presence of an amine proton acceptor such as imidazole in a polar, aprotic solvent such as N,N-dimethylformamide at a temperature range of between about 5° and 40° C., preferably about 25° C., forms a trialkylsilyl hydroxyl-protecting group as shown in formula VII.

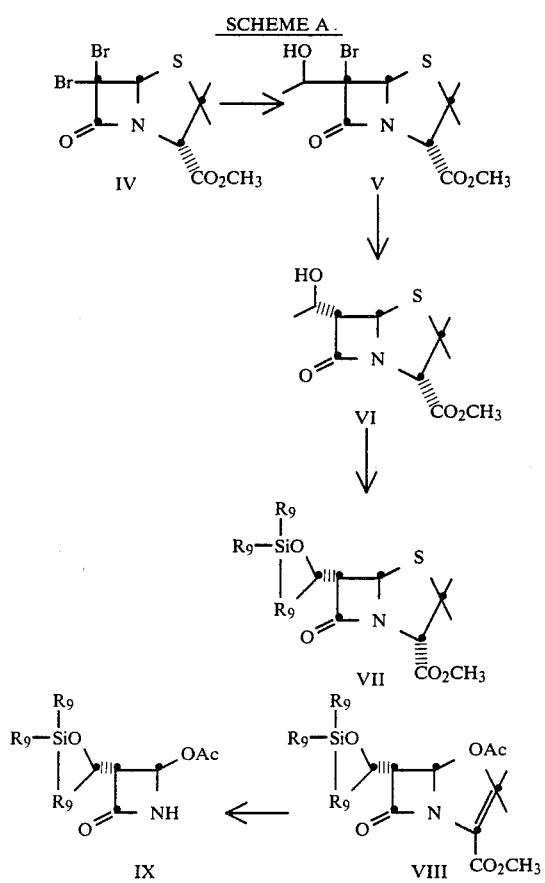

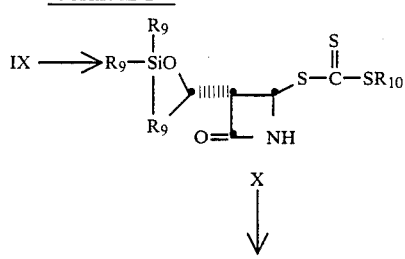

SCHEME B

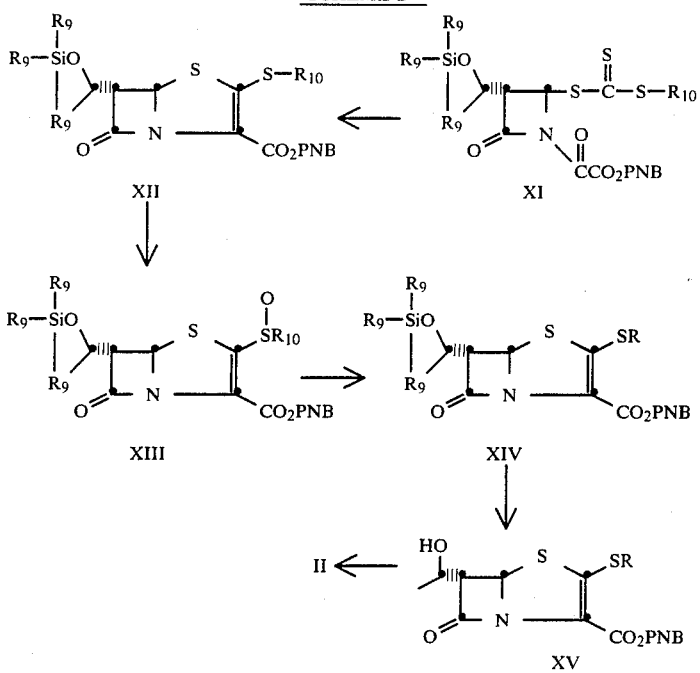

SCHEME C

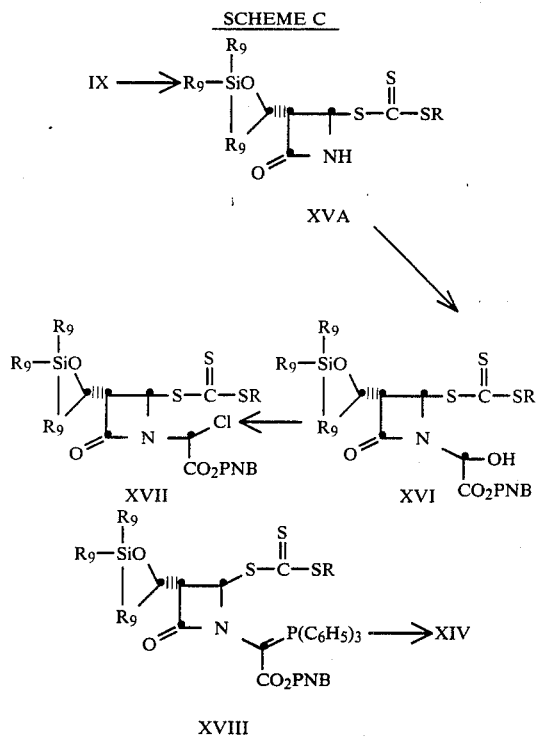

The treatment of VII with mercuric acetate in acetic acid at a temperature of about 90° C. yields the olefin VIII.

In order to obtain the desired azetidinone IX, the olefin VIII is ozonized in a reaction-inert solvent such as dichloromethane at a temperature of between about −80° and −40°, preferably about −78° C. The reaction product is treated with an alkanol such as methanol to yield the azetidine IX.

As shown in Scheme B, a compound of formula IX is treated with trithiocarbonate salt of the formula $M^+R_{10}$—S—C(S)—S$^-$ wherein $R_{10}$ is alkyl having 1–4 carbon atoms, preferably ethyl, and M is a metal such as sodium or potassium to obtain a compound of formula X. This conversion of IX to X is carried out in an organic solvent which is reaction inert, water or a mixture thereof, preferably a mixture of water and dichloromethane at a temperature range of about 0°–35° C., preferably about 25° C.

The compound of formula X is condensed with p-nitrobenzyl chloro-oxalate in the presence of a tertiary alkylamine wherein each alkyl has, for example, 1–4 carbon atoms such as ethyldiisopropylamine, to obtain the compound of formula XI. This condensation reaction is carried out in a reaction-inert solvent, preferably dichloromethane, at a temperature range of about 5–25 ° C., preferably about 10° C.

The resulting compound of formula XI is cyclized using a trialkyl phosphite wherein alkyl has 1–4 carbon atoms, such as triethylphosphite, in a reaction-inert solvent, such as trichloromethane, at a temperature range of about 40°–80° C., preferably about 60° C., to obtain the penem of formula XII.

The thio group of compound XII is oxidized to the corresponding sulfoxide XIII with an oxidizing agent such as m-chloroperbenzoic acid, in a reaction inert solvent such as dichloromethane, at a temperature range of about −10° to −30° C., preferably −20° C.

The sulfoxide XIII is substituted with the mercaptide of formula R—S$^-$ by employing, for example, the sodium or potassium salt which is reacted with the sulfoxide XIII in a polar organic solvent such as ethanol or acetonitrile, at a temperature range of about −50° to −10° C., preferably about −35° C.

Starting mercaptans of the formula R—SH or starting thioacetates of the formula R—S—C(O)CH$_3$ are known for many of the values of R and those which are not known can be prepared by analogous methods known in the art. For a review see J. L. Wardell, "Preparation of Thiols," in *The Chemistry of the Thiol Group*, S. Patai, editor, John Wiley & Sons, London, 1974, Chapter 4. See also Volante, *Tetrahedron Letters*, 22, 3119–3122(1981) for the conversion of alcohols to thiols and thiolesters using triphenylphosphine and a dialkyl azodicarboxylate in the presence of the alcohol and an appropriate thiolacid.

For compounds of formula XIV the trialkylsilyl group is preferably removed prior to the hydrogenolysis to remove the acid-protecting group (PNB) to obtain a compound of formula XV. The trialkylsilyl group is removed with a tetraalkylammonium fluoride in a ethereal solvent such as tetrahydrofuran at a temperature range of about 15° to 40° C., preferably about 25° C.

Conversion of a compound of formula XV to a compound of formula II is accomplished using a conventional hydrogenolysis reaction, and it is carried out in conventional fashion for this type of transformation. Thus, a solution of a compound of the formula XV is stirred or shaken under an atmosphere of hydrogen, or hydrogen mixed with an inert diluent such as nitrogen or argon, in the presence of a catalytic amount of a noble metal hydrogenolysis catalyst, such as a palladium-on-calcium carbonate or a palladium-on-Celite (a diatomaceous earth) catalyst. Convenient solvents for this hydrogenolysis are lower alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble such as aqueous ethers, for example, aqueous tetrahydrofuran, at a pH of about 7 to 8. The hydrogenolysis is usually carried out at room temperature and at a pressure from about 0.5 to about 5 kg/cm$^2$. The catalyst is usually present in an amount from abot 10 percent by weight based on the starting material up to an amount equal in weight to the starting material, although larger amounts can be used. The reaction commonly takes about one hour after which the compound of the formula II is recovered simply by filtration followed by removal of the solvent in vacuo. If palladium-on-calcium carbonate is used as the catalyst, the product is isolated as the calcium salt and if palladium-on-Celite is employed, the product is isolated as the sodium salt.

The compound of formulas I or II can be purified by conventional methods for beta-lactam compounds. For example, the compound of formula I can be purified by gel filtration on Sephadex, or by recrystallization.

An alternate synthetic procedure is shown in Scheme C. The azetidine of formula IX is reacted with a tri-thiocarbonate of the formula M+R—S—C(S)—S⁻, wherein M is a metal such as sodium or potassium, using the procedure previously described to prepare X.

The resulting trithiocarbonate XVA is treated with (p-nitrobenzyloxycarbonyl)(dihydroxy)methane in an aprotic solvent such as benzene, toluene or dimethylformamide, preferably benzene, at a temperature range of about 25°–110° C., preferably about 80° C. to yield the alcohol of formula XVI.

The corresponding chloride XVII is prepared from the alcohol XVI by treatment with thionyl chloride in a reaction-inert organic solvent, such as dichloromethane, in the presence of a hindered amine which serves as an acid acceptor such as 2,6-lutidine, at a temperature range of about −10° to 75° C., preferably 0° C.

The chloride XVII is reacted with a triarylphosphine such as triphenylphosphine in a reaction-inert solvent such as tetrahydrofuran in the presence of a tertiary amine such as 2,6-lutidine at a temperature of about 25° C., to obtain the compound of formula XVIII which is cyclized by refluxing in an aromatic solvent, such as toluene, to yield the penem of formula XIV.

Trithiocarbonate salts of the formula M+R—S—(C=S)—S⁻ are prepared from the appropriate mercaptan of the formula R—SH or by treatment of a thioacetate of the formula RSC(O)CH$_3$ with an alkaline metal alkoxide followed by carbon disulfide.

By employing the heretofore mentioned procedure of Yoshida et al., the stereochemistry at carbon 6 of the penem as well as the hydroxyethyl group attached to carbon 6 is that shown in formula II. The principal stereochemistry for the product of ring closure using Schemes B or C is that wherein the hydrogen at penem ring position 5 is trans to the hydrogen on carbon 6 and in the alpha configuration. Alternatively the sterochemistry can be described as 5R, 6S; 6-(R)-1-hydroxyethyl.

The compounds of formula I or II are acidic and will form salts with basic agents. Such salts are considered to be within the scope of this invention. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo-[4,3,0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred salts of the compounds of formula I or II are sodium, potassium and calcium salts.

The pharmaceutically acceptable salts of formula I or II are those which are free of significant adverse side-effects at the level of ordinary use and include, e.g., the sodium, potassium or calcium salts thereof.

The in vitro activity of the compounds of the formula I or II and salts thereof can be demonstrated by measuring their minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar as the inocula replicating device. Overnight growth tubes are diluted 100-fold for use as the standard inoculum (20,000–10,000 cells in approxmately 0.002 ml. are placed on the agar surface; 20 ml. of BHI agar/dish). Twelve 2-fold dilutions of the test compound are employed, with initial concentration of the test drug being 200 mcg/ml. Single colonies are disregarded when reading plates after 18 hrs. at 37° C. The susceptibility (MIC) of the test organism is accepted as the lowest concentration of compound capable of producing complete inhibition of growth as judged by the naked eye.

The compounds of formula I or II, and the pharmaceutically-acceptable salts thereof, are suitable for the control of bacterial infections in mammmals, including man, e.g. infections caused by susceptible strains of Staphylococcus aureus.

The compounds of the present invention can be administered orally or parenterally, i.e. intramuscularly, subcutaneously, intraperitoneally or intravenously, alone, or combined with a pharmaceutically-acceptable carrier. The ratio of active ingredient to carrier will depend on the chemical nature, solubility and stability of the active ingredient, as well as the dosage contemplated. The ratio of the pharmaceutically-acceptable carrier to the penem compound will normally be in the range from 1:10 to 4:1. For oral administration, the compounds of this invention can be used in the form of tablets, capsules, lozenges, troches, powders, syrups, elixirs, aqueous solutions and suspensions, and the like. In the case of tablets, carriers which can be used include lactose, sodium citrate and salts of phosphoric acid. Various disintegrants such as starch, and lubricating agents, such as magnesium stearate, sodium lauryl sulfate and talc, are commonly used in tablets. Useful diluents for capsules are lactose and high molecular weight polyethylene glycols. When aqueous suspensions are required for oral use, the active ingredient is combined with emulsifying and suspending agents. Sweetening and/or flavoring agents can be added. For parenteral administration, sterile solutions of the active ingredient are usually prepared, and the pH of the solutions are suitably adjusted and buffered. For intravenous use, the total concentration of solutes should be controlled to render the preparation isotonic.

The prescribing physician will determine the appropriate dose for a given human subject, and this can be expected to vary according to the age, weight, and response of the individual patient, as well as the nature and the severity of the patient's symptoms. The compounds of formula I or II will normally be used orally at dosages in the range from about 10 to about 200 mg. per kilogram of body weight per day, and parenterally at dosages from about 10 to about 400 mg. per kilogram of body weight per day. In some cases it may be necessary to use dosages outside these limits.

The following Examples and Preparations are provided solely for further illustration. Infra-red (IR) spectra were measured either as potassium bromide discs (KBr disc), Nujol mull or as solutions in chloroform ($CHCl_3$), methylene chloride ($CH_2Cl_2$) or dimethyl sulfoxide (DMSO), and diagnostic absorption bands are reported in either microns or wave numbers ($cm^{-1}$). Nuclear magnetic resonance (NMR) spectra were measured for solutions in deuterochloroform ($CDCl_3$), perdeuterowater ($D_2O$) or perdeuterodimethyl sulfoxide (DMSO-$d_6$), or mixtures thereof, and peak positions are expressed in parts per million downfield from tetramethylsilane. The following abbreviations for peak shapes are used: s, singlet; d, doublet; t, triplet; q, quartet; m, multiplet; b, broad; w, weak; c, complex. The abbreviations "ss" and "sss" denote that a particular proton appeared as two or three singlets respectively, owing to the presence of diastereoisomers. Throughout the Examples and Preparations, the abbreviation "PNB" represents the p-nitrobenzyl group.

EXAMPLE 1

Sodium (5R,6S)-6-[(R)-1-Hydroxyethyl]-2-(1,3-dioxacyclohex-5-yl)thio-2-penem-3-carboxylate The pH of a suspension of 41 mg of 10% palladium on diatomaceous earth in 8 ml. distilled water +8 ml. tetrahydrofuran was adjusted to ca. 7.5 with 0.02M aqueous sodium bicarbonate solution. A solution of 41 mg. p-nitrobenzyl(5R,6S)-6[(R)-1-hydroxyethyl]-2-(1,3-dioxacyclohex-5-yl)thio-2-penem-3-carboxylate in 4 ml. tetrahydrofuran and 4 ml. distilled water was added and the resulting mixture was hydrogenated at 55 p.s.i. of hydrogen for 75 min. 40 mg. more 10% palladium on diatomaceous earth was added to the reaction mixture and the pH of the suspension was adjusted to ca. 7.0 with 0.02M aqueous sodium bicarbonate solution. The mixture was hydrogenated at 55 p.s.i. of hydrogen for 75 min., then the catalyst was removed by filtration and the filtrate was concentrated in vacuo to remove tetrahydrofuran. The pH of the resulting aqueous solution was adjusted to 7.0 and the solution was extracted with two 20 ml. portions of ethyl acetate. The aqueous phase was then lyophilized yielding 30 g (96% yield) of the title product as an amorphous solid. The infrared spectrum of the title compound as a Nujol mull had a absorption at 5.67 micron.

The procedures were repeated to obtain the title compound in 85% yield. The spectral date is as follows: NMR($D_2O$,250M$H_2$): 1.29 [3H, d, J=6.5 Hz]; 3.57 [1H, m]; 3.90 [2H, m]; 3:92 [1H, dd, J=6.0, 1.4 Hz]; 4.24 [1H, qd, J=6.5, 6.0 Hz]; 4.29 [2H, m]; 4.86 & 4.94 [2H, both d, $J_{AB}$=6.5 Hz]; and 5.68 [1H, d, J=1.4 Hz]ppm. IR(KBr disc): 3040(b), 2966(b), 2846(w), 1770(s), 1593, 1378, 1295, 1169, 1136, 1053, 1020 and 924 $cm.^{-1}$ UV(-$H_2O$)(extinction coefficient in parentheses): 254(4470) and 320(5240) nanometers. $[\alpha]_D(H_2O)$:+139.0°.

EXAMPLE 2

The procedures of Example 1 were employed using compounds of formula XV to obtain the corresponding compounds of formula II as the sodium salt whose R and infrared spectral properties are as shown in Table 1, with the medium in parentheses.

TABLE 1

| R | IR (microns) | Yield (%) |
|---|---|---|
| 1,3-dioxacyclopent-4-ylmethyl | 5.7 (Nujol mull) | 80 |
| 1,3-dioxacyclopent-2-ylmethyl | 2.93, 5.65 and 6.26 (KBr disc) | 82 |
| 2-oxo-1,3-dioxacyclopent-4-ylmethyl | 2.94, 5.66 and 6.28 (KBr disc) | 71 |

PREPARATION A p-Nitrobenzyl(5R, 6S)-6-[(R)-1-Hydroxyethyl]-2-(1,3-dioxacyclo-hex-5-yl)thio-2-penem-3-carboxylate To a solution of 70 mg. (0.12 mmole) p-nitrobenzyl (5R, 6S)-6-[(R)-1-t-butyldimethylsilyloxyethyl]-2-(1,3- dioxacyclohex-5-yl)thio-2-penem-3-carboxylate in 4 ml. anhydrous tetrahydrofuran was added 0.07 ml. (1.2 mmole) acetic acid and 0.36 ml. (0.36 mmole) of a 1M solution of tetrabutylammonium fluoride in tetrahydrofuran. After stirring 40 hr. at room temperature under nitrogen 40 ml. ethyl acetate was added and the resulting solution was washed with 25 ml. saturated aqueous sodium bicarbonate solution, 25 ml. water and 25 ml. saturated aqueous sodium chloride solution. The ethyl acetate solution was then dried over anhydrous sodium sulfate and concentrated in vacuo. The crude product (70 mg) was chromatographed on silica gel (35 g.), eluting with 2:1 chloroform-ethyl acetate, to yield 46 mg. (82% yield) of the title product.

The infrared spectrum of a dichloromethane solution of the title compound had absorptions at 5.58, 5.91 and 6.58 microns. The 250 MHz NMR spectrum of a perdeuterodimethylsulfoxide solution of the title compound had peaks at 1.17 (d,3H); 3.54 (m, 1H); 3.76–3.95 (c,3H); 4.02 (m,1H); 4.2 (m,2H); 4.82 (q,2H); 5.25 (d,1H); 5.38 (q,2H); 5.78 (d,1H); 7.7 (d,2H); and 8.25 (d,2H) ppm.

The procedure was repeated to obtain the title compound in 94% yield, mp: 214°–215° C. (from tetrahydrofuran). The spectral data is as follows: NMR(DMSO-$d_6$, 250 MH$_z$) 1.17 [3H, d, J=6 Hz]; 3.53 [1H, m]; 3.82 [2H, m]; 3.90 [1H, dd, J=6, 1Hz]; 4.01 [1H, m]; 4.20 [2H, m]; 4.79 & 4.83 [2H, both d, $J_{AB}$=6 Hz]; 5.26 [1H, d, J=Hz]; 5.31 & 5.45 [2H, both d, $J_{AB}$=14 Hz]; 5.78 [1H, d, J=1 Hz]; 7.69 [2H, d, J=9 Hz]; and 8.24 [2H, d, J=9 Hz]ppm. IR(KBr disc): 3452, 2965, 2851(w), 1776(S), 1693(S) 1609(w), 1520, 1502, 1376, 1220, 1194, 1176, 1135, 1119, 1047, and 1023 cm.$^{-1}$

PREPARATION B

The procedures of Preparation A were employed using compounds of formula XIV to obtain the corresponding compounds of formula XV whose R, yield and spectral properties, with solvent in parentheses, are shown in Table 2.

TABLE 2

| R | IR (microns) | NMR (ppm) | Yield (%) |
|---|---|---|---|
| 1,3-dioxacyclopent-4-ylmethyl | 5.59, 5.92 and 6.58 (CH$_2$Cl$_2$) | 1.24 (d,3H); 3.0–3.27 (m,2H); 3.48–4.4 (c,6H) 4.83 (s,1H); 5.0 (s,1H); 5.3 (g,2H); 5.6 (d,1H); 7.55 (d,2H); and 8.12 (d,2H).(CDCl$_3$) | 69 |
| 1,3-dioxacyclopent-2-ylmethyl | 5.58, 5.92 and 6.57 (CH$_2$Cl$_2$) | 1.26 (d,3H); 3.18 (d,2H); 5.64–4.5 (c,6H); 5.0 (t,1H); 5.3 (g,2H); 5.6 (d,1H); 7.6 (d,2H); and 8.2 (d,2H), (CDCl$_3$) | 25 |
| 2-oxo-1,3-dioxacyclopent-4-ylmethyl | 5.58, 5.92 and 6.58 (CH$_2$Cl$_2$) | 1.26 (d,3H); 2.96 (d,2H); 3.7 (m,1H); 4.0–5.0 (c,4H); 5.3 (g,2H); 5.62 (d,1H); 7.58 (d,2H); and 8.18 (d,2H).(CDCl$_3$) | 52 |

PREPARATION C p-Nitrobenzyl (5R,6S)-6-[(R)-1-t-Butyldimethylsilyloxyethyl]-2-(1,3-dioxacyclohex-5-yl)thio-2-penem-3-carboxylate Sodium methoxide (27 mg., 0.5 mmole) was added to a solution of 1,3-dioxacyclohex-5-yl thioacetate (81 mg., 0.5 mmole) in 5 ml. anhydrous ethanol cooled to −35° C. under nitrogen. After 45 min. at −35° C., a solution of 300 mg. (ca. 0.5 mmole) crude p-nitrobenzyl (5R,6S)-6-[(R)-1-t-butyldimethylsilyloxyethyl]-2-ethylsulfinyl-2-penem-3-carboxylate in 5 ml. tetrahydrofuran which had been cooled to −50° C. was added. The resulting solution was stirred at −35° C. for 60 min., then 0.029 ml. (0.5 mmole) acetic acid was added and the solution was concentrated in vacuo. The residue was dissolved in 50 ml. ethyl acetate and the resulting solution was washed sequentially with 25 ml. saturated aqueous sodium bicarbonate solution, 25 ml. water and 25 ml. saturated aqueous sodium chloride solution. The ethyl acetate layer was dried over anhydrous sodium sulfate and concentrated in vacuo. Chromatography of the crude product (360 mg.) on silica gel (100 g.), eluting with chloroform, yielded 70 mg. (24% yield) of the title product as a viscous gum.

The infrared spectrum of the title compound in a dichloromethane solution had absorptions at 5.59, 5.9 and 6.57 microns. The NMR spectrum of the title compound in a deuterochloroform solution had peaks at 0.03 (s,3H); 0.06 (s,3H); 0.8 (s,9H); 1.25 (d,3H); 3.4–3.86 (c,4H), 4.0–4.5 (c,3H); 4.63 (d,1H); 4.95 (d,1H); 5.27 (q,2H); 5.63 (d,1H); 7.56 (d,2H); and 8.18 (d,2H) ppm.

The procedure was repeated to obtain the title compound in 65% yield, m.p.: 133°–134° C. (from diethyl ether/petroleum ether). The spectral data is as follows: NMR(CDCl$_3$, 250 MH$_2$): 0.04 [3H, s]; 0.07 [3H, s]; 0.83 [9H, s]; 1.26 [3H, d, J=6.3 Hz]; 3.5–3.75 [3H, m]; 3.75 [1H, dd, J=4.0, 1.5 Hz]; 4.2–4.4 [3H, m]; 4.67 & 4.97 [2H, both d, $J_{AB}$=6.2 Hz]; 5.21 & 5.42 [2H, both d, $J_{AB}$=13.7 Hz]; 5.67 [1H, d, J=1.5 Hz]; 7.61 [2H, d, J=8.7 Hz]; and 8.21 [2H, d, J=8.7 Hz]ppm. IR(KBr disc): 2946, 2927, 2850, 1797(S), 1697(S), 1610, 1512, 1374, 1345, 1320, 1230, 1189, 1168, 1122, 1064, 1025, 982, 931, 835, 801, and 772 cm.$^{-1}$

PREPARATION D

The procedures of Preparation C were employed using the appropriate thioacetate to obtain the corresponding compound of formula XIV where R, yield and spectral properties, with solvent in parentheses, are shown in Table 3.

TABLE 3

| R | IR (microns) | NMR (ppm) | Yield (%) |
|---|---|---|---|
| 1,3-dioxacyclopent-4-ylmethyl | 5.6, 5.92 and 6.57 (CH$_2$Cl$_2$) | 0.03 (s,3H); 0.06 (s,3H); 0.83 (s,9H); 1.23 (d,3H); 2.97–3.22 (m,2H); 3.5–4.4 (c,5H); 4.83 (s,1H); 5.02 (s,1H); 5.26 (g,2H); 5.6 (d,1H); 7.54 (d,2H); and 8.13 (d,2H) (CDCl$_3$) | 37 |
| 1,3-dioxacyclopent-2-ylmethyl | 5.58, 5.9 and 6.57 (CH$_2$Cl$_2$) | 0.03 (s,3H); 0.06 (s,3H), 0.82 (s,9H), | 41 |

TABLE 3-continued

| R | IR (microns) | NMR (ppm) | Yield (%) |
|---|---|---|---|
| | | 1.24 (d,3H); 3.17 (d,2H); 3.63–4.5 (c,5H); 5.02 (t,1H); 5.3 (g,2H); 5.62 (d,1H); 7.58 (d,2H); and 8.18 (d,2H) (CDCl$_3$) | |
| 2-oxo-1,3-dioxacyclopent-4-yl-methyl | 5.58, 5.9 and 6.57 (CH$_2$Cl$_2$) | 0.02 (s,3H); 0.06 (s,3H); 0.82 (s,9H); 1.23 (d,3H); 2.92 (d,2H); 3.7 (m,1H); 4.0–5.0 (c,4H); 5.25 (g,2H); 5.6 (d,1H); 7.53 (d,2H); and 8.14 (d,2H); (CDCl$_3$) | 27 |

PREPARATION E p-Nitrobenzyl (5R,6S)-6-[(R)-1-t-Butyldimethylsilyloxyethyl]-2-ethyl-sulfinyl-2-penem-3-carboxylate A solution of 970 mg. (4.78 mmoles, 85% purity) m-chloroperbenzoic acid in 25 ml. methylene chloride was added to a solution of 2.5 g. (4.78 mmoles) of p-nitrobenzyl (5R,6S)-6-[(R)-1-t-butyldimethylsilyloxyethyl]-2-ethylthio-2-penem-3-carboxylate in 125 ml. methylene chloride cooled to −20° C. under a nitrogen atmosphere. The mixture was stirred at −20° C. for 3 hr., then washed sequentially with two 70 ml. portions of saturated aqueous sodium bicarbonate solution, 70 ml. water and 70 ml. saturated aqueous sodium chloride solution. The methylene chloride solution was dried with anhydrous sodium sulfate and concentrated in vacuo to a yellow foam of the title compound (2.2 g., 86% yield).

The infrared spectrum of the title compound as a dichloromethane solution had absorptions at 5.54, 5.86 and 6.53 microns. The NMR spectrum of the title compound as a deuterochloroform solution had peaks at 0.06, 0.08, 0.1 and 0.12 (4s, total 6H); 0.8(s, 9H); 1.12–1.58 (m, 6H); 3.1 (m, 2H); 3.86(m, 1H), 4.3(m, 1H), 5.3 (m, 2H); 5.67 and 5.78 (2d, total 1H); 7.54(d, 2H); and 8.18 (d, 2H)ppm.

PREPARATION F p-Nitrobenzyl (5R,6S)-6-[(R)-1-t-Butyldimethylsilyloxylethyl]-2-ethylthio-2-penem-3-carboxylate p-Nitrobenzyl oxalyl chloride (5.85 g. 0.024 mole) was added to a mixture of 7.3 g (0.02 mole) (3-alpha-t-butyldimethylsilyloxyethyl-4-ethylthio(thiocarbonyl)thio-2-oxo-azetidine and 4.8 g. (0.048 mole) calcium carbonate in 70 ml. methylene chloride cooled to 10° C. under a nitrogen atmosphere. A solution of 4.17 ml. (0.024 mole) diisopropylethylamine in 20 ml. methylene chloride was added dropwise at a rate to keep the temperature below 12° C. The mixture was stirred for 60 min. at 10° C., then washed with two 50 ml. portions of ice cold water, dried over anhydrous sodium sulfate and concentrated in vacuo to a viscous oil. The resulting crude p-nitrobenzyl (3-alpha-t-butyldimethylsilyloxyethyl-2-oxo-azetidinyl)oxoacetate was dissolved in 300 ml. ethanol-free chloroform and the resulting solution was refluxed under nitrogen while a solution of 6.85 ml. (0.04 mole) triethylphosphite in 50 ml. ethanol-free chloroform was added dropwise over 2 hr. The resulting solution was refluxed for 16 hr., then concentrated in vacuo. The residue was chromatographed on silica gel (800 g.), eluting with 95:5 toluene-ethyl acetate to yield 5.5 g. (53% yield) of the title compound as a yellow foam.

The infrared spectrum of the title compound as a dichloromethane solution had absorptions at 5.56, 5.89 and 6.54 microns. The NMR spectrum of the title compound as a deuterochloroform solution had peaks at 0.07(s,3H); 0.1(s,3H); 0.85(s,9H); 1.12–1.53(m,6H); 2.97(q,2H); 3.7(m,1H); 4.25(m,1H); 5.3(q,2H); 5.63 (d,1H); 7.38(d,2H); and 8.18(d,2H)ppm.

The NMR spectrum of the intermediate 4-ethylthio (thiocarbonyl)thio azetidinone as a deuterochloroform solution had peaks at 0.06(s,6H); 0.8(s,9H); 1.14–1.62(m,6H); 3.14–3.63(m,3H); 4.33(m,1H); 5.16(s,2H); 6.7(d,1H); 7.5(d,2H); and 8.17(d,2H)ppm.

PREPARATION G 3-alpha-t-Butyldimethylsilyloxyethyl-4-ethylthio (thiocarbonyl)thio-2-oxo-azetidine Ethanethiol (8.5 ml. 0.115 mole) was added to a solution of 4.18 g. (0.104 mole) sodium hydroxide in 250 ml. water cooled to 0°–5° C. under a nitrogen atmosphere. After 15 min. 7.73 ml. (0.12 mole) carbon disulfide was added and the mixture was stirred at 0°–5° C. for 35 min. A solution of 15.0 g. (0.0522 mole) 4-acetoxy-3-t-butyldimethylsilyloxyethyl-2-azetidinone in 500 ml. methylene chloride was added and the mixture was stirred vigorously at room tempature for 24 hr. The aqueous phase was separated and extracted with two 150 ml. portions of methylene chloride. The combined methylene chloride fractions were washed with two 200 ml. portions of water and 200 ml. saturated aqueous sodium chloride solution, dried over anhydrous sodium sulfate and concentrated in vacuo. The crude title product (18 g.) was chromatographed on silica gel (500 g.), eluting with 99:1 chloroform-ethyl acetate to yield 9.1 g. (48% yield) of title trithiocarbonate as a yellow foam.

The infrared spectrum of the title compound in dichloromethane solution had absorptions at 5.62 and 9.2 microns. The NMR spectrum of a deuterochloroform solution of the title compound had peaks at 0.08(s,6H); 0.8(s,9H); 1.02–1.5(m,6H); 3.0–3.48(m,3H); 4.12(m,1H); 5.54(d,1H); and 6.57(b,1H)ppm.

PREPARATION H 1,3-Dioxacyclohex-5-yl p-Toluenesulfonate p-Toluenesulfonyl chloride (38.1 g, 0.2 mole) was added to a solution of 20.8 g (0.2 mole) glycerol formal (a mixture comprised of 67% 1,3-dioxan-5-ol and 33% (1,3-dioxolan-4-yl)methanol) in 200 ml. pyridine cooled to 0° C. under nitrogen. The reaction mixture was stirred at 0° C. for ½ hr., then at 25° C. for 20 hr. The mixture was added to 500 ml. 6N aqueous hydrochloric acid solution and the resulting mixture was extracted with four 200 ml. portions of ethyl acetate. The combined ethyl acetate extracts were washed with two 200 ml. portions of 1N aqueous hydrochloric acid solution, two 200 ml. portions of water and 200 ml. saturated aqueous sodium chloride solution, dried over anhydrous sodium sulfate and concentrated in vacuo to an oil. The crude product was dissolved in 500 ml. di-isopropyl ether whereupon the desired 1,3-dioxacyclohex-5-yl tosylate crystallized. Filtration yielded 17.4 g of white crystalline tosylate, m.p. 91°–92° C. Another 4.3 g of crystalline tosylate was obtained from the mother liquors (total yield 42%). The NMR spectrum of the title compound as a deuterochloroform solution had peaks at 2.45 (s,3H); 3.54–4.13 (c,4H); 4.26–4.6 (m,1H), 4.75 (s,2H); 7.3 (d,2H); and 7.8 (d, 2H) ppm.

PREPARATION I

1,3-Dioxacyclopent-4-ylmethyl p-Toluenesulfonate p-Toluenesulfonyl chloride (76.2 g, 0.4 mole) was added to a solution of 104.1 g (1 mole) glycerol formal (a mixture comprised of 67% 1,3-dioxacyclohex-5-ol and 33% (1,3-dioxacyclopent-4-yl)methanol) in 1000 ml. pyridine cooled to 0° C. under nitrogen. After standing at 0° C. for 20 hr. the reaction mixture was allowed to warm to room temperature and added to 1500 ml. of 6N aqueous hydrochloric acid. The resulting mixture was extracted with four 500 ml. portions of ethyl acetate. The combined ethyl acetate extracts were washed with two 500 ml. portions of 6N aqueous hydrochloric acid solution, two 500 ml. portions of water and 500 ml. saturated aqueous sodium chloride solution, dried over anhydrous sodium sulfate and concentrated in vacuo. The oily product (78.4 g) consisted of ca a 2:1 mixture of 1,3-dioxacyclopent-4-ylmethyl tosylate and 1,3-dioxacyclohex-5-yl tosylate which was used without purification in a subsequent step (Preparation K).

PREPARATION J

1,3-Dioxacyclohex-5-yl Thioacetate

A solution of 28.0 g (0.108 mole) 1,3-dioxacyclohex-5-yl p-tosylate and 24.6 g (0.216 mole) potassium thioacetate in 500 ml. dimethylformamide was heated at 80° C. under nitrogen for 20 hr. The reaction mixture was then cooled to room temperature and diluted with 1000 ml. water. The resulting mixture was extracted with six 300 ml. portions of ethyl acetate. The combined ethyl acetate extracts were washed with four 500 ml. portions of water and 500 ml saturated aqueous sodium chloride solution, dried over anhydrous sodium sulfate and concentrated in vacuo to an oil. Distillation of the product yielded 6.25 g (36% yield) of the title thioacetate, bp 70° C. (0.4 mm.).

The NMR spectrum of the title compound as a deuterochlorform solution had the peaks at 2.34 (s,3H); 3.4–4.36 (c,5H); and 4.8 (q,2h) ppm.

The procedure was repeated to obtain the title compound in 49% yield, bp 85°–89° C. (0.7mm). NMR(CDCl$_3$, 250 MH$_2$): 2.34 (3H, s); 3.7–3.85 (3H, m); 4.05–4.2 (2H, m); 4.79 (1H, d, Jgem=6.2 Hz); and 4.89 (1H, d, Jgem=6.2 Hz) ppm.

PREPARATION K

(1,3-Dioxacyclopent-4-yl)methyl Thioacetate

A mixture of 78 g. (0.3 mole) 1,3-dioxacyclopent-4-yl tosylate (from Preparation I) and 27.4 g. (0.24 mole) potassium thioacetate in 1500 ml. acetone was refluxed under nitrogen overnight. The reaction mixture was then concentrated in vacuo and the residue was dissolved in 500 ml. ethyl acetate +500 ml. water. The aqueous layer was extracted with 500 ml. ethyl acetate. The combined ethyl acetate extracts were washed with two 500 ml. portions of water and 500 ml. saturated aqueous sodium chloride solution, dried over anhydrous sodium sulfate and concentrated in vacuo. The residue, which consisted of a solid suspended in an oil, was filtered. The filtrate was distilled under reduced pressure, yielding 20.8 g. (54%) of 1,3-dioxacyclopent-4-ylmethyl tosylate, bp 65°–70° (0.2 mm).

The solid product was washed with ether to yield 18.4 g of 1,3-dioxacyclohex-5-yl tosylate.

The NMR spectrum of the title compound as a deuterochloroform solution showed peaks at 2.37 (s,3H); 3.1 (d,2H); 3.4–4.4 (c,3H); 4.86 (s,H); and 5.02 (s,1H) ppm.

PREPARATION L

(1,3-Dioxacyclopent-2-yl)methyl Thioacetate

A mixture of 5.0 g. (0.03 mole) 2-bromomethyl-1,3-dioxacyclopentane and 5.13 g. (0.045 mole) potassium thioacetate in 60 ml. acetone was refluxed under nitrogen overnight. The mixture was filtered and the filtrate was concentrated in vacuo. The residue was partitioned between 100 ml. ethyl acetate and 60 ml. water. The aqueous layer was extracted with 50 ml. ethyl acetate and the combined ethyl acetate portions were washed with 50 ml. water and 50 ml. saturated aqueous sodium chloride solution. The ethyl acetate solution was dried over anhydrous sodium sulfate and concentrated in vacuo. The residue was chromatographed on silica gel, eluting with methylene chloride to yield 4.0 g (83% yield) of the desired thioacetate as an oil.

The NMR spectrum of the title compound as a deuterochloroform solution had peaks at 2.36 (s,3H); 3.16 (d,2H); 3.94 (c,4H); and 5.0 (t,1H) ppm.

PREPARATION M

2-Oxo-1,3-dioxacyclopent-4-ylmethyl Thioacetate

Di-isopropyl azodicarboxylate (3.9 ml., 0.02 mole) was added to a solution of 5.2 g (0.02 mole) triphenylphosphine in 50 ml. anhydrous tetrahydrofuran cooled to 0° C. under nitrogen. The solution was stirred at 0° for 30 min., during which time a precipitate formed. To this mixture was added dropwise at 0° a solution of 1.18 g. (0.01 mole) glycerine carbonate and 1.4 ml (0.02 mole) thioacetic acid in 20 ml. anhydrous tetrahydrofuran. The mixture was stirred at 0° for 1 hr., then at room temperature for 2 ½ hr. The mixture was concentrated in vacuo and the residue was partitioned between 70 ml. ethyl acetate and 70 ml. water. The ethyl acetate layer was washed with two 50 ml. portions of saturated aqueous sodium bicarbonate solution, 50 ml. water and 50 ml. saturated aqueous sodium chloride solution, dried over anhydrous sodium sulfate and concentrated in vacuo. The residue was chromatographed on silica gel, eluting with methylene chloride to yield 600 mg. of impure material. Further purification of the impure product by chromatography on silica gel and eluting with 3:1 hexane/ethyl acetate yielded 220 mg. (13% yield) of the desired thioacetate as an oil.

The NMR spectrum of the title compound as a deuterochlorform solution had peaks at 2.4 (s,3H); 3.25 (d,2H); and 3.94–5.07 (c,3H) ppm.

I claim:
1. A compound of the formula

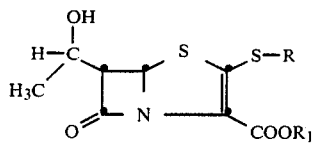

or a pharmaceutically acceptable salt thereof, wherein R is

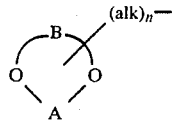

A is carbonyl, thiocarbonyl or methylene;
B is alkylene having 2-5 carbon atoms;
alk is alkylene having 1-6 carbon atoms;
$R_1$ is hydrogen or a group which results in an ester which is hydrolyzable in vivo; and
n is zero or one.

2. A compound according to claim 1 wherein $R_1$ is hydrogen.
3. A compound according to claim 2 wherein B is ethylene.
4. A compound according to claim 3 wherein A is methylene.
5. A compound according to claim 4 wherein n is one.
6. A compound according to claim 5 wherein alk is methylene.
7. A compound according to claim 6 wherein R is 1,3-dioxacyclopent-4-ylmethyl.
8. A compound according to claim 6 wherein R is 1,3-dioxacyclopent-2-ylmethyl.
9. A compound according to claim 3 wherein A is carbonyl.
10. A compound according to claim 9 wherein n is one.
11. A compound according to claim 10 wherein alk is methylene.
12. A compound according to claim 11 wherein R is 2-oxo-1,3-dioxacyclopent-4-ylmethyl.
13. A compound according to claim 2 wherein B is propylene.
14. A compound according to claim 13 wherein A is methylene.
15. A compound according to claim 14 wherein n is zero.
16. A compound according to claim 15 wherein R is 1,3-dioxacyclohex-5-yl.
17. A compound according to claim 13 wherein A is carbonyl.
18. A compound according to claim 17 wherein n is zero.
19. A compound according to claim 18 wherein R is 2-oxo-1,3-dioxacyclohex-5-yl.
20. A pharmaceutical composition for use in the treatment of a bacterial infection in a mammal comprising a compound according to claim 1 and a pharmaceutically acceptable diluent or carrier.
21. A method of treating a bacterial infection in a mammal comprising administering an antibacterially effective amount of a compound according to claim 1.
22. A compound of the formula

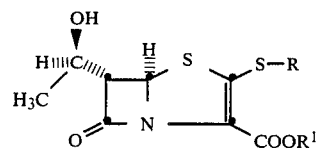

or a pharmaceutically acceptable salt thereof, wherein R is

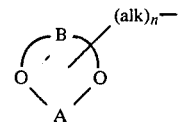

A is carbonyl, thiocarbonyl or methylene;
B is alkylene having 2-5 carbon atoms;
alk is alkylene having 1-6 carbon atoms;
$R_1$ is hydrogen or a group which results in an ester which is hydrolyzable in vivo; and
n is zero or one.

23. A compound according to claim 22 wherein $R_1$ is hydrogen.
24. A compound according to claim 23 wherein B is ethylene.
25. A compound according to claim 24 wherein A is methylene.
26. A compound according to claim 25 wherein n is one.
27. A compound according to claim 26 wherein alk is methylene.
28. A compound according to claim 27 wherein R is 1,3-dioxacyclopent-4-ylmethyl.
29. A compound according to claim 27 wherein R is 1,3-dioxacyclopent-2-ylmethyl.
30. A compound according to claim 24 wherein A is carbonyl.
31. A compound according to claim 30 wherein n is one.
32. A compound according to claim 31 wherein alk is methylene.
33. A compound according to claim 32 wherein R is 2-oxo-1,3-dioxacyclopent-4-ylmethyl.
34. A compound according to claim 23 wherein B is propylene.
35. A compound according to claim 34 wherein A is methylene.
36. A compound according to claim 35 wherein n is zero.
37. A compound according to claim 36 wherein R is 1,3-dioxacyclohex-5-yl.
38. A compound according to claim 34 wherein A is carbonyl.
39. A compound according to claim 38 wherein n is zero.
40. A compound according to claim 39 wherein R is 2-oxo-1,3-dioxacyclohex-5-yl.
41. A pharmaceutical composition for use in the treatment of a bacterial infection in a mammal comprising a compound according to claim 22 and a pharmaceutically acceptable diluent or carrier.
42. A method of treating a bacterial infection in a mammal comprising administering an antibacterially effective amount of a compound according to claim 22.

* * * * *